United States Patent [19]

Ambrogi et al.

[11] 4,002,750
[45] Jan. 11, 1977

[54] PYRAZINE 4-OXIDE DERIVATIVES AND PROCESS FOR THEIR PREPARATION

[75] Inventors: Vittorio Ambrogi; Willy Logemann; Marc Antonio Parenti; Raffaele Tommasini, all of Milan, Italy

[73] Assignee: Carlo Erba S.p.A., Milan, Italy

[22] Filed: May 19, 1975

[21] Appl. No.: 578,820

Related U.S. Application Data

[63] Continuation of Ser. No. 354,909, April 26, 1973, abandoned.

[30] Foreign Application Priority Data

Apr. 28, 1972 Italy .................................. 23663/72

[52] U.S. Cl. .............................. 424/250; 260/250 B
[51] Int. Cl.² ....................................... C07D 241/24
[58] Field of Search ................. 260/250 B; 424/250

[56] References Cited

FOREIGN PATENTS OR APPLICATIONS 4,420,345  2/1969  Japan ............................ 260/250 B

OTHER PUBLICATIONS

Litmanowitsch et al., Chemical Abstracts, vol. 70, 20,083c (1969).

Beilstein, vol. 25, pp. 126–127 (1936).

*Primary Examiner*—Donald G. Daus
*Assistant Examiner*—Jose Tovar
*Attorney, Agent, or Firm*—Murray and Whisenhunt

[57] ABSTRACT

Compounds of the formula (I)

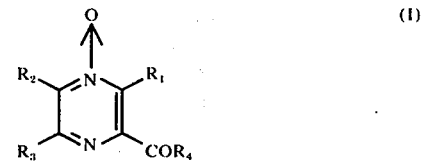

are disclosed, wherein at least one of $R^1$, $R^2$ and $R^3$ is $C_{1-6}$ alkyl and the others are hydrogen atoms; $R^4$ is hydroxy or $C_{1-6}$ alkoxy, or a salt of the compound wherein $R^4$ is hydroxy with a pharmaceutically acceptable base. A typical compound is, for example, 2-carboxy-5-methylpyrazine 4-oxide.

These compounds exhibit hypoglycaomic and hypolipaomic activity.

17 Claims, No Drawings

PYRAZINE 4-OXIDE DERIVATIVES AND PROCESS FOR THEIR PREPARATION

This is a continuation division of application Ser. No. 354,909 filed Apr. 26. 1973, now abandoned.

This invention relates to new pyrazine derivatives having hypoglycaemic and hypolipaemic activity, to a process for their preparation, and to pharmaceutical compositions containing them.

The use of the nicotinic acid and related compounds is known in hypolipaemic therapy [Altschul, Hoffer and Stephen, Arch. Biochem. Biophys., 1955, 54, 558]. However, at the beginning of the treatment, the use of the nicotinic acid constantly causes undesired peripheral vasodilatory effects, which persist in 10 – 15% of patients after the initial period even if with lower intensity. It is advisable, anyway, not to use this product in patients with a history of peptic ulcers, diabetes or hyperuricaemia; in fact, at the dose administered, the nicotinic acid may cause gastrointestinal troubles, hypoxglycaemia, hyperuricaemia and liver function disorders.

We have now found that replacing the pyridine nucleus of nicotinic acid by the pyrazine nucleus, it is possible to obtain compounds with hypoglycaemic and hypolipaemic activity which do not cause the side-effects caused by the pyridine derivatives.

The invention provides a compound a general formula (I)

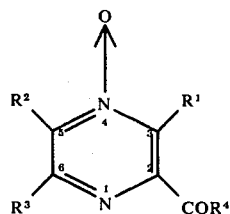

wherein each of $R^1$, $R^2$ and $R^3$, which may be the same or different, in a hydrogen or halogen atom or a $C_{1-6}$ alkyl or alkoxy group, at least one of $R^1$, $R^2$ and $R^3$ being other than a hydrogen atom; $R^4$ is a hydroxy or $C_{1-6}$ alkoxy group or a group of formula—$NR^5R^6$ wherein each of $R^5$ and $R^6$, which may be the same or different, is a hydrogen atom or a $C_{1-6}$ alkyl group; or, when $R^4$ is a hydroxy group, a pharmaceutically acceptable salt of said compound.

Preferably at least one of $R^1$, $R^2$ and $R^3$ is a methyl group, and the others are hydrogen atoms.

The alkyl groups may be branched or unbranched.

The salts can be with a suitable organic or inorganic base. The preferred salt is with ethanolamine.

The compounds can be prepared by a process comprising oxidising a compound of general formula (II)

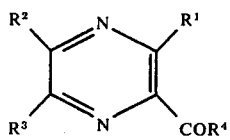

wherein $R^1$, $R^2$, $R^3$ and $R^4$ are as defined above, and then if desired converting by methods known per se the compound of general formula (I) so produced into another compound of general formula (I), and if desired, when $R^4$ is a hydroxy group, reacting the compound of general formula (I) with a base to give a pharmaceutically acceptable salt.

For example, a compound of general formula (I), wherein $R^4$ is a hydroxy group can be converted into a compound of general formula (I), wherein $R^4$ is an alkoxy group or a —$NR^5R^6$ group; or a compound of general formula (I), wherein $R^4$ is an alkoxy group or a —$NR^5R^6$ group can be converted into a compound of general formula (I), wherein $R^4$ is a hydroxy group; or a compound of formula (I), wherein $R^4$ is an alkoxy group, may be converted into a compound of general formula (I), wherein $R^4$ is a —$NR^5R^6$ group. A compound of general formula (I), wherein $R^4$ is a —$NR^5R^6$ group, wherein one or both of $R^5$ and $R^6$ are hydrogen atoms can be converted into a compound of general formula (I) wherein $R^4$ is a —$NR^5R^6$ group wherein one or both of $R^5$ and $R^6$ are alkyl groups.

The compounds of general formula (II), wherein $R^4$ is a hydroxy group, are known compounds and can be prepared by methods known per se. For example, 2-carboxy-5-methylpyrazine may be obtained by oxidising 5-methyl-2-hydroxymethylpyrazine with potassium permanganate, according to Pitré, Boveri and Grabitz, Chem. Ber., 1966, 99, 364. The compounds of general formula (II), wherein $R^4$ is an alkoxy group may be prepared from the compounds of general formula (II), wherein $R^4$ is a hydroxy group by esterification according to the usual methods of organic chemistry. The compounds of general formula (II), wherein $R^4$ is a —$NR^5R^6$ group, may be prepared from the compounds of general formula (II), wherein $R^4$ is a hydroxy or alkoxy group, by the usual methods of organic chemistry, for example by reacting a compound of general formula

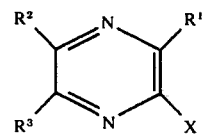

wherein X is a carboxy group or a functional derivative thereof, e.g. a halide or a mixed anhydride, with ammonia or an amine of formula $NHR^5R^6$.

The oxidation of the compounds of general formula (II) is preferably performed with peracids, which may be prepared in situ. The preferred peracids are peracetic, m-chloro perbenzoic and penmaleic acid. When the oxidation is performed on a compound of general formula (II), wherein $R^4$ is a hydroxy group, the carboxy group is preferably protected in a conventional way, i.e. by using one of the protecting groups commonly employed for this purpose in organic chemistry. For example, the methyl and ethyl esters may be conveniently used as protecting groups; those protecting groups which can be removed under mild reaction conditions, e.g. benzyl, t-butyl, p-methoxybenzyl or phthalimidomethyl esters, can also be used.

The conversion of the compound of general formula (I), wherein $R^4$ is a hydroxy group into a compound of general formula (I), wherein $R^4$ is an alkoxy group, may be performed by methods known per se, for example by adding dry hydrogen chloride to a solution of the starting material in methyl alcohol or absolute ethyl alcohol, heating it in a sealed tube with methanol or ethanol and thionyl chloride, or treating wich a diazoalkane, e.g. diazomethane.

The conversion of the compound of general formula (I), wherein $R^4$ is a hydroxy group into a compound of general formula (I), wherein $R^4$ is a —$NR^5R^6$ group can be performed by methods known per se such as activating the carboxy group (e.g. by forming a mixed anhydride or active ester) and reacting it with ammonia or an amine of formula $NHR^5R^6$. The conversion of the compounds of general formula (I), wherein $R^4$ is an alkoxy group or a —$NR^5R^6$ into a compound of general formula (I), wherein $R^4$ is a hydroxy group, may be also performed by means of methods known per se, for example by saponification with an aqueous alkali or by hydrolysis.

The conversion of a compound of general formula (I), wherein $R^4$ is an alkoxy group, into a compound of general formula (I), wherein $R^4$ is a —$NR^5R^6$ group, may be performed by methods known per se, for example by refluxing with concentrated ammonia or with an amine of general formula $NHR^5R^6$.

Finally, the conversion of a compound of general formula (I), wherein $R^4$ is a —$NR^5R^6$ group wherein one or both of $R^5$ and $R^6$ are hydrogen atoms, into a compound of general formula (I) wherein one or both of $R^5$ and $R^6$ are alkyl groups, may be performed by methods known per se, for example by alkylation with an alkyl halide in dimethylsulphoxide in the presence of powdered potassium hydroxide.

The compounds of general formula (I) have hypoglycaemic and hypolipaemic activity, as is shown by the tests reported in the following Table, in which the values given in brackets indicate the times (in minutes) at which the highest effects were observed.

TABLE

| Compound (50 mg/kg dose in rats) | Percentage glycaemic lowering in comparison with controls after the same time | Effect on free fatty acids. Percentage lowering in comparison with controls after the same time |
| --- | --- | --- |
| 2-Carbamayl-1,5-methyl-pyrazine 4-oxide | 24% (90–120 min.) | 73% (60 min.) 79% (90 min.) |
| 2-(N,N-diethylcarbamoyl)-5-methyl-pyrazine 4-oxide | 25% (60 min.) | 84.2% (60 min.) 71.3% (120 min.) |
| 2-Carboxy-5-methyl-pyrazine 4-oxide | 28.6% (120 min.) | 84.6% (60 min.) 85% (120 min.) |

The activity of these compounds was evaluated on groups of six "outbred" SPF CFB rats each weighing 140 – 160 g. The animals were fasted but allowed to drink water 18 hours before the test. For each compound tested, three groups of animals were treated and sacrificed after 60, 120 and 240 minutes, respectively. The test substances were administered at a dose of 50 mg/kg by gavage, suspended in 0.5% methylcellulose 400, the dose not exceeding the volume of 0.2 ml/100 g. The sodium nicotinate was used as a reference substance at the same dose. Groups of animals treated only with the suspending agent acted as controls. At the indicated times, the animals were decapitated. Their blood was immediately cooled and centrifuged. The glycaemic titres and level of free fatty acids were evaluated in plasma. The glycaemic values were determined by the o-toluidine method according to Wenk, Creno, Loock and Henry, Clin. Chem., 1969, 15, (12). The plasma free fatty acids were determined according to Trout's modification of Dole's method (Trout, Estes and Friedberg, J. Lipid, Res., 1960, 1, 199 – 202).

The invention also provides a pharmaceutical composition comprising a compound of general formula (I) and a pharmaceutically acceptable carrier or diluent.

The compounds of the present invention can be conveniently incorporated with pharmaceutical carriers or diluents such as, for instance, gelatine capsules; microcrystalline cellulose; lactose; natural gums; starches, such as corn starch and potato starch; cellulose derivatives, such as sodium carboxymethyl cellulose, ethyl cellulose, methyl cellulose, cellulose acetate phthalate; gelatin; talc; stearic acid; magnesium stearate; as well as other non-toxic compatible substances used in pharmaceutical formulations.

The compositions are preferably in a form suitable for oral administration, for example tablets, capsules, liquid solutions or suspensions.

The invention is illustrated by the following Examples.

EXAMPLE 1

2-Carboxy-5-methylpyrazine (9.7 g) in dry dioxan (114 ml) and tributylamine (17.7 ml) was treated with ethyl chloroformate (7.5 ml), keeping the temperature at 0°–5° C. After ten minutes, dioxan (190 ml) saturated with ammonia was added. The mixture was stirred for 3 hours at room temperature, then dioxan was distilled off, and the residue was taken up in saturated aqueous sodium bicarbonate (20 ml). The mixture was filtered and the product washed with water to give 2-carbamoyl-5-methylpyrazine (9.2 g), m.p. 204°–206° C. This amide (7 g) in glacial acetic acid (30 ml) and 35% hydrogen peroxide (20 ml.) was heated with stirring at 70° C for 7 hours. The reaction mixture was cooled, the product which separated was filtered and washed with water to give 2-carbamoyl-5-methylpyrazine 4-oxide (5.5 g), m.p. 206°–208° C.

Preceding in the same way, 2-carboxy-5,6-dimethylpyrazine gave 2-carbamoyl-5,6-dimethylpyrazine 4-oxide (m.p. 248°–249° C), while 2-carboxy-6-methylpyrazine-2-carboxylic acid gave 2carbamoyl-6-methylpyrazine 4-oxide (m.p. 225° C).

EXAMPLE 2

2-Carboxy-5-methylpyrazine (9.4 g) suspended in methylene chloride (100 ml) was treated with triethylamine (9.8 ml). The mixture was cooled to 0°– 5° C, ethyl chloroformate (7.4 ml) was added dropwise, and, after ten minutes, diethylamine (9.48 ml) was added. The mixture was stirred for 5 hours at room temperature, the triethylamine hydrochloride so obtained was filtered, the methylene chloride distilled off and the crude diethylamide so obtained was oxidised. The crude diethylamide (3.5 g) was added to glacial acetic acid (107 ml)/30% hydrogen peroxide (7.25 ml.). The reaction mixture was heated at 70° C for 6½ hr., then cooled and the product that separated was filtered to give 2-(N,N-diethylcarbamoyl)-5-methylpyrazine 4-oxide (2.5 g) m.p. 110°–112° C.

In the same way 2-carboxy-5-methylpyrazine and monoethylamine were converted to 2-(N-ethylcarbamoyl)-5-methylpyrazine 4-oxide (m.p. 191°–193° C).

EXAMPLE 3

2-Carbamoyl-5-methylpyrazine 4-oxide (5 g) was added to 10% sodium hydroxide (50 ml) and then refluxed for 30 minutes. The reaction mixture was acidified with dilute hydrochloric acid and extracted in a continuous extractor with ethyl acetate. The ethyl acetate extract was concentrated to small volume and gave, after filtration 2-carboxy-5-methylpyrazine 4-oxide 3.2 g), m.p. 178°–180° C.

Proceeding in the same way 2-carbamoyl-6-methylpyrazine 4-oxide gave 2-carboxy-6-methylpyrazine 4-oxide (m.p. 187°–190° C), while 2-carbamoyl-5,6-dimethylpyrazine 4-oxide gave 2-carboxy-5,6-dimethylpyrazine 4-oxide (m.p. 177°–180° C).

EXAMPLE 4

2-Carboxy-5-methylpyrazine 4-oxide (2.5 g) was added to methanol (60 ml) and ethanolamine (1.1 ml). The mixture was refluxed for 20 minutes, then cooled and filtered to obtain 2-carboxy-5-methylpyrazine 4-oxide ethanolamine salt (2.1 g), m.p. 177°–180° C, after crystallisation from methanol.

In the same way, 2-carboxy-5,6-dimethylpyrazine 4-oxide and ethanolamine were converted to 2-carboxy-5,6-dimethylpyrazine 4-oxide ethanolamine salt, m.p. 178°–180° C.

EXAMPLE 5

2-Carboxy-5-methylpyrazine 4-oxide (6.5 g) was heated in a sealed tube with absolute ethanol (15 ml) and thionyl chloride (1 ml) for 5 hours at 60° C to give 2-carboxy-5-methylpyrazine 4-oxide ethyl ester (4 g).

EXAMPLE 6

2-Carboxy-5,6-dimethylpyrazine 4-oxide ethyl ester (5 g) was refluxed with 28 Be ammonium hydroxide (20 ml) to give 2-carbamoyl-5,6-dimethylpyrazine 4-oxide (3.5 g), m.p. 248°–249° C.

EXAMPLE 7

2-Carboxy-5-methylpyrazine 4-oxide ethyl ester (4.5 g) was added to 10% sodium hydroxide (45 ml) and the mixture was refluxed for 5 hours. The reaction mixture was acidified with dilute hydrochloric acid and extracted in a continuous extractor with ethyl acetate. The ethyl acetate extract was concentrated to small volume to give, after filtration 2-carboxy-5-methylpyrazine 4-oxide (3.5 g), m.p. 178°–180° C.

EXAMPLE 8

30% Hydrogen peroxide (40 ml) was added under cooling and with stirring to maleic anhydride (78 g) in chloroform (60 ml). After two hours 2-carboxy-5-methylpyrazine (4.8 g) was added and the mixture kept for two days at 0°–5° C. The maleic acid was filtered off. After concentration to small volume, the produce was treated with ethyl acetate to give, after filtration 2-carboxy-5-methylpyrazine 4-oxide (1.1 g), m.p. 178°–180° C.

EXAMPLE 9

A. 2-Carboxy-5-methylpyrazine potassium salt (6 g) suspended in dimethylformamide (80 ml) was treated with p-methoxybenzyl bromide (8 g). After 12 hours, the mixture was poured into water-ice; the aqueous solution was extracted with chloroform, washed with saturated sodium bicarbonate and then with water. Drying gave 2-carboxy-5-methylpyrazine p-methoxybenzyl ester (10 g).

B. The product (4.5 g) of (A) in chloroform (100 ml) was treated dropwise with 90% m-chloroperbenzoic acid (3.32 g) in chloroform (100 ml). After four hours, the reaction mixture was washed with saturated sodium bicarbonate and then with water. Drying over sodium sulphate and then under reduced pressure gave 2-carboxy-5-methylpyrazine 4-oxide p-methoxybenzyl ester (3.8 g).

C. The product (3 g) of (B) was treated with trifluoroacetic acid (3 ml) and benzene (30 ml). The mixture was stirred for 1 hour at room temperature and the benzene and the trifluoroacetic acid were removed under reduced pressure. The residue was treated with water, and the pH brought to 3. Extraction with ethyl acetate, concentration and filtration gave 2-carboxy-5-methylpyrazine 4-oxide (1.6 g), m.p. 178°–180° C.

EXAMPLE 10

Powdered potassium hydroxide (1.7 g) was added to 2-carbamoyl-5-methylpyrazine 4-oxide (4 g) in dimethyl sulphoxide (20 ml). Ethyl bromide (6.55 g) was added dropwise with cooling; after 4 hours, water (80 ml) was added, and the precipitate was filtered to give 2-(N,N-diethylcarbamoyl)-5-methylpyrazine 4-oxide (2.8 g), m.p. 110°–112° C.

What we claim is:

1. A compound of formula (I)

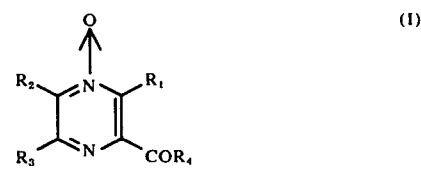

wherein at least one of $R^1$, $R^2$ and $R^3$ is $C_{1-6}$ alkyl and the others are hydrogen atoms; $R^4$ is hydroxy or $C_{1-6}$ alkoxy, or a salt of the compound wherein $R^4$ is hydroxy with a pharmaceutically acceptable base.

2. A compound of the formula

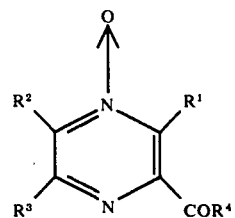

wherein $R^2$ is $C_1$-$C_6$ alkyl, and $R^1$ and $R^3$ are hydrogen; $R^4$ is hydroxy or $C_1$-$C_6$ alkoxy, or a salt of the compound wherein $R^4$ is hydroxy with a pharmaceutically acceptable base.

3. A compound according to claim 1 wherein at least one of $R^1$, $R^2$ and $R^3$ is a methyl group and the others are hydrogen atoms.

4. A compound according to claim 2 in the form of an ethanolamine salt.

5. 2-Carboxy-5-methylpyrazine 4-oxide.

6. 2-Carboxy-6-methylpyrazine 4-oxide.

7. 2-Carboxy-5,6-dimethylpyrazine 4-oxide.

8. 2-Carboxy-5-methylpyrazine 4-oxide ethanolamine salt.

9. 2-Carboxy-5,6-dimethylpyrazine 4-oxide ethanolamine salt.

10. 2-Carboxy-5-methylpyrazine 4-oxide ethyl ester.

11. 2-carboxy-5-methylpyrazine 4-oxide methyl ester.

12. Compound of claim 2, wherein $R^2$ is methyl.

13. Compound of claim 12, wherein $R^4$ is hydroxy or a salt thereof with a pharmaceutically acceptable base.

14. A pharmaceutical composition consisting essentially of a compound according to claim 1 and a pharmaceutically acceptable carrier or diluent.

15. Composition of claim 14, wherein said compound is a compound of claim 2.

16. Composition of claim 14, wherein said compound is compound of claim 13.

17. Compound of claim 1, wherein $R^4$ is hydroxy or a salt thereof with a pharmaceutically acceptable base.

* * * * *